(12) United States Patent
Heaton et al.

(10) Patent No.: US 7,736,673 B2
(45) Date of Patent: Jun. 15, 2010

(54) STABILIZED PHARMACEUTICAL PRODUCT

(75) Inventors: Zoe Heaton, Cheshire (GB); David Goodwin, Holmes Chapel (GB); Iain Breakwell, Cheshire (GB)

(73) Assignee: Nycomed GmbH, Constance (DE)

( * ) Notice: Subject to any disclaimer, the term of this patent is extended or adjusted under 35 U.S.C. 154(b) by 76 days.

(21) Appl. No.: 11/259,495

(22) Filed: Oct. 26, 2005

(65) Prior Publication Data

US 2006/0147537 A1   Jul. 6, 2006

Related U.S. Application Data

(63) Continuation of application No. PCT/GB2004/002249, filed on May 27, 2004.

(30) Foreign Application Priority Data

May 28, 2003   (GB) ................. 0312148.0

(51) Int. Cl.
   A61K 9/14    (2006.01)
   A01N 45/00   (2006.01)
   A61K 31/715  (2006.01)

(52) U.S. Cl. .................. 424/489; 514/171; 514/53; 514/61

(58) Field of Classification Search ............... 424/489; 514/171, 53, 61
   See application file for complete search history.

(56) References Cited

U.S. PATENT DOCUMENTS

| | | | |
|---|---|---|---|
| 5,263,475 A | 11/1993 | Dubach et al. |
| 5,482,934 A | 1/1996 | Calatayud et al. |
| 5,709,884 A | 1/1998 | Trofast et al. |
| 6,040,344 A | 3/2000 | Gao et al. |
| 6,268,533 B1 | 7/2001 | Gao et al. |
| 6,472,563 B1 | 10/2002 | Tanoury et al. |
| 6,475,467 B1 | 11/2002 | Keller et al. |
| 6,645,466 B1 | 11/2003 | Keller et al. |
| 2001/0038858 A1 | 11/2001 | Roser et al. |
| 2002/0053344 A1 * | 5/2002 | Davies et al. ........ 128/203.15 |
| 2002/0183293 A1 | 12/2002 | Banerjee et al. |
| 2004/0231666 A1 | 11/2004 | Barker |
| 2006/0104917 A1 | 5/2006 | Wayland et al. |

FOREIGN PATENT DOCUMENTS

| | | |
|---|---|---|
| DE | 19541689 | 5/1996 |
| JP | 2004051502 | 2/2004 |

(Continued)

OTHER PUBLICATIONS

Lee Kirsch et al., Development of a Lyophilized Formulation for (R,R)-Formoterol (L)-Tatrate; Drug Dev. and Indust. Pharm., 2001, v. 27, pp. 89-91.

(Continued)

*Primary Examiner*—Robert A Wax
*Assistant Examiner*—Aradhana Sasan
(74) *Attorney, Agent, or Firm*—The Nath Law Group; Joshua B. Goldberg; Sheldon M. McGee

(57) ABSTRACT

The invention relates to the use of an adsorbent and a sealed package, for example an overwrap, to protect a pharmaceutical product in a solid state in the presence of a reducing sugar.

33 Claims, 2 Drawing Sheets

FOREIGN PATENT DOCUMENTS

| | | |
|---|---|---|
| WO | WO 96/31198 | 10/1996 |
| WO | WO 98/31351 | 7/1998 |
| WO | WO 00/21487 | 4/2000 |
| WO | WO 00/28979 | 5/2000 |
| WO | WO 00/32170 | 6/2000 |
| WO | WO 01/32163 | 5/2001 |
| WO | WO 01/39745 | 6/2001 |
| WO | WO 01/89491 | 11/2001 |
| WO | WO 01/89492 | 11/2001 |
| WO | WO 01/89616 | 11/2001 |
| WO | WO 01/98174 | 12/2001 |
| WO | WO 01/98175 | 12/2001 |
| WO | WO 02/28368 | 4/2002 |
| WO | WO 03/043905 | 5/2003 |
| WO | WO 03/086349 | 10/2003 |
| WO | WO 2004/052374 | 6/2004 |
| WO | WO 2004/103379 | 12/2004 |
| WO | WO 2004/110460 | 12/2004 |
| WO | WO 2005/007853 | 1/2005 |
| WO | WO 2005/034911 | 4/2005 |
| WO | WO 2005/034927 | 4/2005 |

OTHER PUBLICATIONS

Gotz, English Translation of DE 195 41 689 A1.

* cited by examiner

STABILIZED PHARMACEUTICAL PRODUCT

FIELD OF THE INVENTION

This invention relates to a stabilized pharmaceutical product comprising a medicament. More particularly, it relates to a package and packaging method that utilizes an adsorbent material, such as a molecular sieve, that adsorbs or absorbs moisture in the inner local environment of an impermeable package, so as to prevent formation of Maillard products which result from chemical reactions between the medicament and a reducing sugar in the medical device in the presence of moisture. It also relates to a method of substantially maintaining the fine particle fraction of a medicament.

BACKGROUND OF THE INVENTION

Formoterol drug substances are known to be stable at ambient conditions for up to two years. However, when Formoterol is mixed with lactose degradation is known to occur (Maillard reaction) because of interactions between the amino groups within the Formoterol molecule and the lactose moiety.

Accordingly, what is needed is a stable pharmaceutical product in which the formation of Maillard degradation products are reduced or eliminated in order to preserve the efficacy of the medicament contained within the pharmaceutical product.

The citation of any reference herein should not be construed as an admission that such reference is available as "Prior Art" to the instant application.

SUMMARY OF THE INVENTION

Provided herein is a novel and useful stable pharmaceutical product in which the degradation of a medicament contained therein as a result of a Maillard reaction between the medicament and a pharmaceutically acceptable carrier, e.g. a reducing sugar, is reduced or eliminated.

Broadly, the present invention extends to a stable pharmaceutical product that comprises (a) a pharmaceutical composition in the solid state, which comprises a medicament and a reducing sugar, (b) an effective amount of an adsorbent material, and (c) a sealed package that is substantially impermeable to moisture, wherein the sealed package has an enclosed volume within which the pharmaceutical composition and the adsorbent material are situated. The pharmaceutical composition may be housed in a dry powder inhaler that is located within the sealed package.

Furthermore, the present invention extends to a stable pharmaceutical product comprising:
a) a pharmaceutical composition in the solid state comprising formoterol and a reducing sugar;
b) an effective amount of an adsorbent material;
c) a sealed package substantially impermeable to moisture, wherein the sealed package has an enclosed volume within which the pharmaceutical composition and the adsorbent material are situated.

The present invention also extends to a stable pharmaceutical product comprising:
a) a pharmaceutical composition in the solid state comprising formoterol fumarate dihydrate and non-micronized lactose monohydrate, wherein the pharmaceutical composition is housed within a dry powder inhaler;
b) an effective amount of an adsorbent material;
c) a sealed package substantially impermeable to moisture, wherein the sealed package has an enclosed volume within which the dry powder inhaler and the adsorbent material are situated.

Moreover, the present invention extends to a stable pharmaceutical product comprising:
a) a pharmaceutical composition in the solid state comprising formoterol fumarate dihydrate and non-micronized lactose monohydrate, wherein the pharmaceutical composition is housed within a dry powder inhaler;
b) an effective amount of an adsorbent material;
c) a sealed package substantially impermeable to moisture, wherein the sealed package is a flexible laminate forms an enclosed volume within which the dry powder inhaler and the adsorbent material are situated.

The present invention further extends to method for preventing the formation of one or more Maillard products in a pharmaceutical product, due to a chemical reaction between a medicament of the pharmaceutical product and a reducing sugar, wherein the pharmaceutical product comprises:
a) a pharmaceutical composition in the solid state comprising the medicament and a reducing sugar;
b) an effective amount of an adsorbent material;
c) a sealable package substantially impermeable to moisture, wherein the sealable package has an enclosed volume within which the pharmaceutical composition and the adsorbent material are situated;
wherein the method comprises the steps of:
(i) positioning an effective amount of the adsorbent material and the pharmaceutical composition within a sealable package;
(ii) sealing the sealable package so that the pharmaceutical composition and adsorbent are in an enclosed volume within the package; and
adsorbing moisture in the package so as to prevent the formation of one or more Maillard products.

Numerous types of medicaments for treating a respiratory disease or disorder have applications in a pharmaceutical composition of a stable pharmaceutical product or in a method of the present invention for preventing the formation of one or more Maillard products in a pharmaceutical product. An example of such a medicament is an anti-inflammatory, which includes corticosteroids such as mometasone furoate, triamcinalone acetonide, flunisolide, fluticasone propionate, budesonide, beclomethasone dipropionate, prednisone, betamethasone, cortisone, dexamethasone, hydrocortisone, methylprednisolone, prednisolone, and ciclesonide, to name only a few, a mast cell stabilizer such as Intal, Tilade, etc., and leukotriene modifier medicament including, but certainly not limited to zafirlukast, montelukast sodium, and zileuton. Another example of an applicable medicament is a beta2-agonist, which includes, but certainly is not limited to salmeterol xinafoate, formoterol, albuterol, and salmeterol. Still another example is an anticholinergic, e.g. ipratropium bromide, tiotropium bromide, etc. Respiratory diseases or disorders that can be treated with a stable pharmaceutical product or a method for preventing the formation of one or more Maillard products in a pharmaceutical product of the present invention include, but certainly are not limited to asthma and Chronic Obstructive Pulmonary Disease (COPD). Moreover, a pharmaceutical composition can comprise a medicament alone or in combination with another medicament.

Naturally, various sizes of the particles of a medicament in a stable pharmaceutical product of the present invention or a method of the present invention for preventing the formation of one or more Maillard products in a pharmaceutical product have applications herein. In particular, the size of the particles can be about 0.1 μm to about 10 μm. In a particular embodiment of a stable pharmaceutical product or a method for preventing formation of one or more Maillard products of the present invention, greater than about 95% of a medicament has a particle size of less than about 5 µm.

The present invention also extends to a method for substantially maintaining the fine particle fraction of a hydrophilic medicament in a pharmaceutical composition, comprising the steps of:

(a) providing a pharmaceutical product that comprises:
(i) the pharmaceutical composition comprising the medicament and a reducing sugar;
(ii) an effective amount of an adsorbent material;
(iii) a sealed package substantially impermeable to moisture having an enclosed volume within which the pharmaceutical composition and the adsorbent material are situated; and (b) contacting the hydrophilic medicament in the pharmaceutical composition with a hydrophobic material, wherein the ratio of the hydrophobic material to the hydrophilic medicament is at least 5:1.

Numerous hydrophilic medicaments have applications in a method for substantially maintaining fine particle fraction of the present invention. Examples include, but certainly are not limited to a beta2-agonist, such as salmeterol xinafoate, formoterol, and albuterol, to name only a few. Likewise, numerous hydrophobic materials have applications herein, including, but not limited to hydrophobic medicaments for treating a respiratory disease or disorder such as an anti-inflammatory, e.g. a corticosteroid such as mometasone furoate, flunisolide, triamcinalone acetonide, fluticasone propionate, budesonide, beclomethasone dipropionate, prednisone, betamethasone, cortisone, dexamethasone, hydrocortisone, methylprednisolone, prednisolone, ciclesonide, etc. In a particular embodiment, the hydrophilic medicament is formoterol and the hydrophobic material is ciclesonide. In another particular embodiment, the hydrophilic medicament is formoterol, and the hydrophobic medicament is a corticosteroid selected from the group consisting of mometasone furoate, flunisolide, triamcinalone acetonide, fluticasone propionate, budesonide, beclomethasone dipropionate, prednisone, betamethasone, cortisone, dexamethasone, hydrocortisone, methylprednisolone, and prednisolone.

Furthermore, as disclosed above, the ratio of hydrophobic medicament present to hydrophilic material present in a method for substantially maintaining fine particle fraction is at least 5:1. In a particular embodiment though, the ratio is about 10:1 to about 100:1.

In addition, particle size of the hydrophobic material and the hydrophilic medicament used in a method for substantially maintaining fine particle fraction of the present invention can vary, i.e. about 0.1 µm to about 10 µm. More particularly, greater than about 95% of the particles have a size of less than about 5 µm.

Furthermore, in a stable pharmaceutical product or in a method of the present invention as described herein, the adsorbent material can be located in a variety of places. For example, the adsorbent material can be situated in the enclosed volume between the package and dry powder inhaler, should it be present. Should the pharmaceutical composition be housed within a dry powder inhaler, the adsorbent material may also be located within the dry powder inhaler. Another option is to have the adsorbent material incorporated into a polymer mixture used to produce the dry powder inhaler. As a result, the adsorbent material is manufactured into a plastic component of the dry powder inhaler. Other locations at which the adsorbent material can be placed is into the sealed package, or even incorporated into an adhesive used to seal the sealed package, e.g. in a self-adhesive patch or tape. In a particular embodiment of a stable pharmaceutical product or a method of the present invention, the adsorbent material is located within in a porous sachet that, in turn, is located within the sealed package.

Naturally, numerous adsorbent materials have applications in a stable pharmaceutical product or a method of the present invention, including a molecular sieve, an activated clay, charcoal, an activated alumina, silica, a zeolite, a bauxite, or any mixture of these materials, to name only a few. In particular embodiment of a stable pharmaceutical product or a method of the present invention, the adsorbent material is a 10 Å (Angstrom) molecular sieve. An effective amount of the adsorbent material used in a stable pharmaceutical product or in a method of the present invention is that amount sufficient to reduce or eliminate the formation of Maillard products. One of ordinary skill can readily determine this amount for a particular embodiment of the present invention using routine laboratory techniques.

Moreover, a sealed package of a stable pharmaceutical product or a method of the present invention can be produced from a variety of materials, e.g. metal, glass, plastic, etc. Similarly, the shape of a sealed package can vary. Examples of such shapes include, but certainly are not limited to bottle, a bag, a drum box, and an irregularly shaped container. In a particular embodiment of a stable pharmaceutical product or a method of the present invention, the sealed package is made from a flexible laminate that comprises a protective outer layer, a heat sealable layer, and a moisture impermeable layer located between the protective outer layer and the heat sealable layer. Generally, an adhesive such as a polyester adhesive is located between each of the layers. Numerous materials can be used for the protective layer, including paper or a polymer, such as polyester. Likewise, the moisture impermeable layer can be made of a variety of materials, such as a polymer or a metal, e.g. aluminum, copper, steel, zinc, iron, tin, magnesium an amalgam, etc., to name only a few. The heat sealable layer can also be made of a variety of materials that can undergo heat sealing. In a particular embodiment of a stable pharmaceutical product or a method of the present invention, the flexible laminate comprising a polyester layer, an aluminum layer, and a polyethylene layer, wherein the aluminum layer is located between the polyester and polyethylene layers. The sealing of a package of a stable pharmaceutical product or a method of the present invention can be accomplished in a variety of ways. More specifically, heat-sealing, gluing, welding, brazing, mechanical closures, mechanical clamps, or compression can hermetically seal a sealed package of a stable pharmaceutical product of the present invention or a method of the present invention.

Furthermore, various reducing sugars (as well as hydrates thereof) have applications in a stable pharmaceutical product or a method of the present invention, e.g. lactose, glucose, mannose, galactose, maltose, xylose, cellobiose, mellibiose, and maltotriose, to name only a few. In particular, a reducing sugar having applications herein is lactose. More particularly, the reducing sugar is lactose monohydrate. A particular grade of lactose monohydrate having applications herein is RESPITOSE ML001 (DMV, Veghel, The Netherlands). Moreover, a reducing sugar having applications herein need not be micronised. In a particular embodiment, the reducing sugar has a mean particle size of about 41 µm. In addition, a reducing sugar of a stable pharmaceutical product or a method of the present invention can be non-micronized.

Moreover, in a particular embodiment of a stable pharmaceutical product or a method of the present invention, wherein a medicament is formoterol and the reducing sugar is lactose monohydrate, a pharmaceutical composition comprises about 2969 µg to about 3016 µg of lactose monohydrate per about 0.5 µg to about 4 µg of formoterol. In a more particular embodiment, a pharmaceutical composition comprises about 2969 µg to about 3016 µg of lactose monohydrate per about 1 µg to about 2 µg of formoterol; and in a still more particular embodiment, a pharmaceutical composition comprises about 2969 µg to about 3016 µg of lactose monohydrate per about 1 µg of formoterol.

Accordingly, it is an aspect of the present invention to provide a stable pharmaceutical product comprising a medicament in which formation Maillard products will be reduced or prevented.

It is another aspect of the present invention to provide a method for protecting the fine particle fraction of a medicament for pulmonary delivery to a patient.

These and other aspects of the present invention will be better appreciated by reference to the following drawings and Detailed Description.

DETAILED DESCRIPTION OF THE INVENTION

Figure 1:
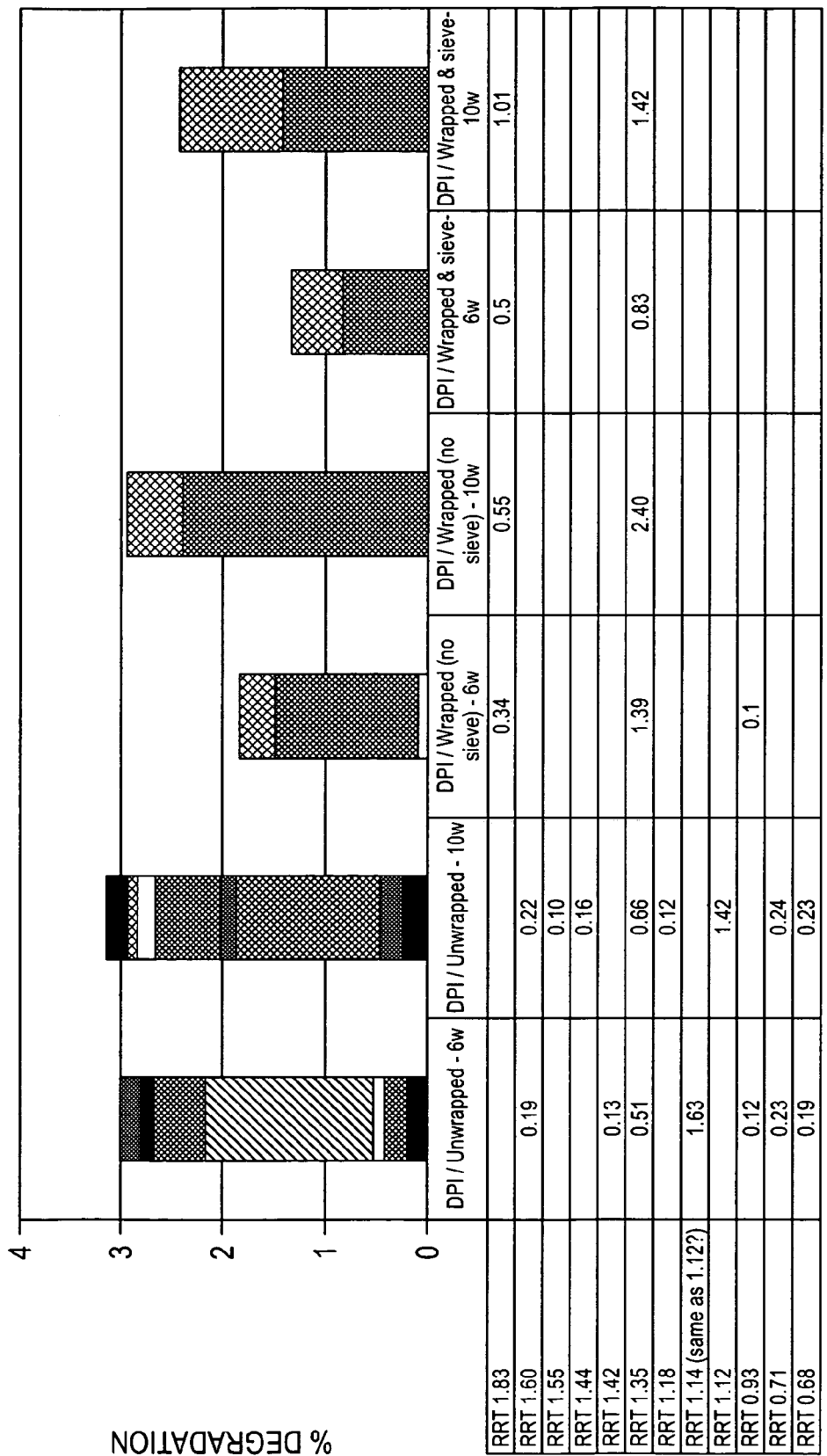
FIG. 1 is a bar chart that shows an impurities comparison of a dry powdered inhaler (DPI) comprising Ciclesonide, Formoterol and lactose, wherein the DPI is wrapped, wrapped in the presence of molecular sieves, and unwrapped, at 6 and 10 weeks at 40 degrees Celsius and 75% relative humidity.

[1] A stable pharmaceutical product comprising:
 a) a pharmaceutical composition in the solid state comprising a medicament and a reducing sugar;
 b) an effective amount of an adsorbent material; and
 c) a sealed package substantially impermeable to moisture having an enclosed volume within which the pharmaceutical composition and the adsorbent material are situated.

[2] The stable pharmaceutical product according to embodiment [1], further comprising a dry powder inhaler that houses the pharmaceutical composition.

[3] The stable pharmaceutical product according to embodiment [2], wherein the adsorbent material is situated in the enclosed volume between the sealed package and the dry powder inhaler.

[4] The stable pharmaceutical product according to embodiment [2], wherein the dry powder inhaler houses the adsorbent material.

[5]. The stable pharmaceutical product according to embodiment [2], wherein the adsorbent material is incorporated into a polymer mixture and manufactured into a plastic component of the dry powder inhaler.

[6] The stable pharmaceutical product according to either of embodiments [1] or [2], wherein the adsorbent material is incorporated into the sealed package.

[7] The stable pharmaceutical product according to any one of embodiments [1] to [4], wherein the adsorbent material is incorporated into an adhesive.

[8] The stable pharmaceutical product according to embodiment [7], wherein the adhesive is a self-adhesive patch or a tape.

[9]. The stable pharmaceutical product according to any one of embodiments [1] to [4], wherein the adsorbent material is in a porous sachet.

[10] The stable pharmaceutical product according to any one of embodiments [1] to [9], wherein the adsorbent material is selected from the group consisting of a molecular sieve, an activated clay, charcoal, an activated alumina, silica, a zeolite, a bauxite, and a mixture thereof.

[11] The stable pharmaceutical product according to embodiment [10], wherein the adsorbent material is 10 Å (Angstrom) molecular sieves.

[12] The stable pharmaceutical product according to any one of embodiments [1] to [11], wherein the sealed package is made of metal, glass, or plastic, and the sealed package is selected from the group consisting of a bottle, a bag, a drum box, and an irregularly shaped container.

[13] The stable pharmaceutical product according to embodiment [12], wherein the sealed package is a flexible laminate.

[14] The stable pharmaceutical product according to embodiment [13], wherein the flexible laminate comprises three layers: a protective layer, a heat sealable layer, and a moisture impermeable layer located between the protective layer and the heat sealable layer.

[15] The stable pharmaceutical product according to embodiment [14], wherein the protective layer is polyester, the moisture impermeable layer is a metal selected from the group consisting of aluminum, copper, steel, zinc, iron, tin, magnesium, and a mixture thereof, and the heat sealable layer is polyethylene.

[16] The stable pharmaceutical product of embodiment [15], wherein the moisture impermeable layer is aluminum.

[17] The stable pharmaceutical product according to any one of embodiments [1] to [16], wherein the sealed package is hermetically sealed by heat-sealing, gluing, welding, brazing, mechanical closures, mechanical clamps, or compression.

[18] The stable pharmaceutical product according to any one of embodiments [1] to [17], wherein the medicament is used in the treatment of a respiratory disease.

[19] The stable pharmaceutical product according to embodiment [18], wherein the medicament comprises an anti-inflammatory, a beta2-agonist, an anticholinergic, or a combination thereof.

[20] The stable pharmaceutical product of embodiment [19], wherein the anti-inflammatory comprises a corticosteroid, a mast cell stabilizer, or a leukotriene modifier.

[21] The stable pharmaceutical product of embodiment [20], wherein the corticosteroid is selected from the group consisting of mometasone furoate, triamcinalone acetonide, flunisolide, fluticasone propionate, budesonide, beclomethasone dipropionate, prednisone, betamethasone, cortisone, dexamethasone, hydrocortisone, methylprednisolone, and prednisolone.

[22] The stable pharmaceutical product of embodiment [20], wherein the corticosteroid is ciclesonide.

[23]The stable pharmaceutical product of embodiment [20], wherein the mast cell stabilizer comprises intal, tilade, or a combination thereof.

[24] The stable pharmaceutical product of embodiment [20], wherein the leukotriene modifier comprises zafirlukast, montelukast sodium, zileuton, or a combination thereof.

[25] The stable pharmaceutical product according of embodiment [19], wherein the beta2-agonist is selected from the group consisting of salmeterol xinafoate, formoterol, albuterol, and salmeterol.

[26] The stable pharmaceutical product of embodiment [19], wherein the anti-cholinergic is selected from the group consisting of ipratropium bromide, tiotropium bromide, and a mixture thereof.

[27] The stable pharmaceutical product of embodiment [25], wherein the medicament is formoterol.

[28] The stable pharmaceutical product of embodiment [27], further comprising a corticosteroid.

[29] The stable pharmaceutical product according to embodiment [28], wherein the corticosteroid is ciclesonide.

[30] The stable pharmaceutical product according to any one of embodiments [1] to [29], wherein the medicament has a particle size of about 0.1 μm to about 10 μm.

[31] The stable pharmaceutical product according to any one of embodiments [1] to [30], wherein greater than about 95% of the medicament has a particle size of less than about 5 μm.

[32] The stable pharmaceutical product according to any one of embodiments [1] to [31], wherein the reducing sugar is non-micronized.

[33] The stable pharmaceutical product according to any one of embodiments [1] to [32], wherein the reducing sugar has a mean particle size of about 41 μm.

[34] The stable pharmaceutical product according to any one of embodiments [1] to [33], wherein the reducing sugar is selected from the group consisting of lactose, glucose, mannose, galactose, maltose, xylose, cellobiose, mellibiose, and maltotriose.

[35] The stable pharmaceutical product according to any one of embodiments [1] to [34], wherein the reducing sugar is lactose.

[36] The stable pharmaceutical product according to embodiment [35], wherein the reducing sugar is lactose monohydrate.

[37] The stable pharmaceutical product of embodiment [36], wherein the lactose monohydrate is non-micronized.

[38] The stable pharmaceutical product according to either of embodiments [36] or [37], wherein the pharmaceutical composition comprises about 2969 μg to about 3016 μg of lactose monohydrate per about 0.5 μg to about 4 μg of formoterol.

[39] The stable pharmaceutical product according to embodiment [38], wherein the pharmaceutical composition comprises about 2969 μg to about 3016 μg of lactose monohydrate per about 1 μg to about 2 μg of formoterol.

[40] The stable pharmaceutical product according embodiment [39], wherein the pharmaceutical composition comprises about 2969 μg to about 3016 μg of lactose monohydrate per about 1 μg of formoterol.

[41] The stable pharmaceutical product according to any one of embodiments [1] to [40], wherein the effective amount of the adsorbent material is the amount sufficient to prevent or reduce formation of Maillard products.

[42] A stable pharmaceutical product comprising:
  a) a pharmaceutical composition in the solid state comprising formoterol and a reducing sugar;
  b) an effective amount of an adsorbent material; and
  c) a sealed package substantially impermeable to moisture having an enclosed volume within which the pharmaceutical composition and the adsorbent material are situated.

[43] The stable pharmaceutical product of embodiment [42], wherein the formoterol is formoterol fumarate dihydrate.

[44] The stable pharmaceutical product of either of embodiments [42] or [43], wherein the reducing sugar is selected from the group consisting of lactose, glucose, mannose, galactose, maltose, xylose, cellobiose, mellibiose, and maltotriose.

[45] The stable pharmaceutical product of embodiment [44], wherein the reducing sugar is lactose.

[46] The stable pharmaceutical product of embodiment [45], wherein the reducing sugar is lactose monohydrate.

[47] The stable pharmaceutical product of embodiment [46], wherein the lactose monohydrate is non-micronized.

[48] The stable pharmaceutical product according to either of Embodiments [46] or [47], wherein the pharmaceutical composition comprises about 2969 μg to about 3016 μg of lactose monohydrate per about 0.5 μg to about 4 μg of formoterol.

[49] The stable pharmaceutical product according to embodiment [48], wherein the pharmaceutical composition comprises about 2969 μg to about 3016 μg of lactose monohydrate per about 1 μg to about 2 μg of formoterol.

[50] The stable pharmaceutical product according to embodiment [49], wherein the pharmaceutical composition comprises about 2969 μg to about 3016 μg of lactose monohydrate per about 1 μg of formoterol.

[51] The stable pharmaceutical product according to any one of embodiments [42] to [50], wherein the reducing sugar has a mean particle size of about 41 μm.

[52] The stable pharmaceutical product of any of embodiments [42]-[51], wherein the pharmaceutical composition further comprises a second medicament for treating a respiratory disease or disorder.

[53] The stable pharmaceutical product of embodiment [52], wherein the second medicament comprises an anti-inflammatory, a beta2-agonist, an anticholinergic, or a combination thereof.

[54] The stable pharmaceutical product of embodiment [53], wherein the anti-inflammatory comprises a corticosteroid, a mast cell stabilizer, or a leukotriene modifier.

[55] The stable pharmaceutical product of embodiment [54], wherein the corticosteroid is selected from the group consisting of mometasone furoate, triamcinalone acetonide, flunisolide, fluticasone propionate, budesonide, beclomethasone dipropionate, prednisone, betamethasone, cortisone, dexamethasone, hydrocortisone, methylprednisolone, and prednisolone.

[56] The stable pharmaceutical product of embodiment [55], further comprising formoterol.

[57] The stable pharmaceutical product of embodiment [54], wherein the corticosteroid is ciclesonide.

[58] The stable pharmaceutical product of embodiment [57], further comprising a beta2-agonist selected from the group consisting of salmeterol xinafoate, albuterol and salmeterol.

[59]. The stable pharmaceutical product of embodiment [54], wherein the mast cell stabilizer comprises intal, tilade, or a combination thereof.

[60] The stable pharmaceutical product of embodiment [54], wherein the leukotriene modifier comprises zafirlukast, montelukast sodium, or zileuton, or a combination thereof.

[61] The stable pharmaceutical product of embodiment [53], wherein the beta2-agonist is selected from the group consisting of salmeterol xinafoate, formoterol, albuterol, and salmeterol.

[62] The stable pharmaceutical product of embodiment [53], wherein the anticholinergic is selected from the group consisting of ipratropium bromide, tiotropium bromide, and a mixture thereof.

[63] The stable pharmaceutical product according to any one of embodiments [42]-[63], wherein the adsorbent material is selected from the group consisting of a molecular sieve, an activated clay, charcoal, an activated alumina, silica, a zeolite, a bauxite, and a mixture thereof.

[64] The stable pharmaceutical product of embodiment [63], wherein the adsorbent material is 10 Å (Angstrom) molecular sieves.

[65] The stable pharmaceutical product of any of embodiments [42]-[64], further comprising a dry powder inhaler that houses the pharmaceutical composition.

[66] The stable pharmaceutical product according to any one of embodiments [42]-[65], wherein the sealed package is made of metal, glass, or plastic, and the sealed package is selected from the group consisting of a bottle, a bag, a drum box, and an irregularly shaped container.

[67] The stable pharmaceutical product of any of embodiments [42]-[66], wherein the sealed package is a flexible laminate.

[68] The stable pharmaceutical product according to embodiment [67], wherein the flexible laminate comprises three layers: a protective layer, a heat sealable layer, and a moisture impermeable layer located between the protective layer and the heat sealable layer.

[69] The stable pharmaceutical product according to embodiment [68], wherein the protective layer is polyester, the moisture impermeable layer is a metal selected from the group consisting of aluminum, copper, steel, zinc, iron, tin, magnesium, and a mixture thereof, and the heat sealable layer is polyethylene.

[70] The stable pharmaceutical product of embodiment [69], wherein the moisture impermeable layer is aluminum.

[71] The stable pharmaceutical product according to any one of embodiments [42]-[70], wherein the sealed package is hermetically sealed by heat-sealing, gluing, welding, brazing, mechanical closures, mechanical clamps, or compression.

[72] The stable pharmaceutical product according to any one of embodiments [42]-[71] wherein the pharmaceutical composition has a particle size of about 0.1 µm to about 10 µm.

[73] The stable pharmaceutical product according to any one of embodiments [42]-[72], wherein greater than about 95% of the pharmaceutical composition has a particle size of less than about 5µm.

[74] The stable pharmaceutical product of any of embodiments [42]-[73], wherein the effective amount of the adsorbent material is that amount to prevent or reduce formation of Maillard products.

[75] A stable pharmaceutical product comprising:
a) a pharmaceutical composition in the solid state comprising formoterol fumarate dihydrate and non-micronized lactose monohydrate, wherein the pharmaceutical composition is housed within a dry powder inhaler;
b) an effective amount of an adsorbent material;
c) a sealed package substantially impermeable to moisture, wherein the sealed package has an enclosed volume within which the dry powder inhaler and the adsorbent material are situated.

[76] The stable pharmaceutical product of embodiment [75], wherein the pharmaceutical composition further comprises a second medicament for treating a respiratory disease or disorder.

[77] The stable pharmaceutical product of embodiment [76], wherein the second medicament comprises an anti-inflammatory, a beta2-agonist, an anticholinergic, or a combination thereof.

[78] The stable pharmaceutical product of embodiment [77], wherein the anti-inflammatory comprises a corticosteroid, a mast cell stabilizer, or a leukotriene modifier.

[79] The stable pharmaceutical product of embodiment [78], wherein the corticosteroid is selected from the group consisting of mometasone furoate, triamcinalone acetonide, flunisolide, fluticasone propionate, budesonide, beclomethasone dipropionate, prednisone, betamethasone, cortisone, dexamethasone, hydrocortisone, methylprednisolone, and prednisolone.

[80] The stable pharmaceutical product of embodiment [78], wherein the corticosteroid is ciclesonide.

[81] The stable pharmaceutical product of embodiment [78], wherein the mast cell stabilizer comprises intal, tilade, or a combination thereof.

[82] The stable pharmaceutical product of embodiment [78], wherein the leukotriene modifier comprises zafirlukast, montelukast sodium, zileuton, or a combination thereof.

[83] The stable pharmaceutical product according of embodiment [77], wherein the beta2-agonist is selected from the group consisting of salmeterol xinafoate, albuterol, and salmeterol.

[84] The stable pharmaceutical product of embodiment [77], wherein the anticholinergic is selected from the group consisting of ipratropium bromide, tiotropium bromide, and a combination thereof.

[85] The stable pharmaceutical product of any of embodiments or [75]-[84], wherein the pharmaceutical composition has a particle size of about 0.1 µm to about 10 µm.

[86] The stable pharmaceutical product of any of embodiments [75]-[85], wherein greater than about 95% of the pharmaceutical composition has a particle size of less than about 5µm.

[87] The stable pharmaceutical product according to any one of embodiments [75]-[86], wherein the non-micronized lactose monohydrate has a mean particle size of about 41 µm.

[88] The stable pharmaceutical product according to any one of embodiments [75]-[87], wherein the adsorbent material is a 10 Å (Angstrom) molecular sieve.

[89] The stable pharmaceutical product according to any of embodiments [75]-[88], wherein the pharmaceutical composition comprises about 2969 µg to about 3016 µg of lactose monohydrate per about 0.5 µg to about 4 µg of formoterol fumarate dihydrate.

[90] The stable pharmaceutical product according to embodiment [89], wherein the pharmaceutical composition comprises about 2969 µg to about 3016 µg of lactose monohydrate per from about 1 µg to about 2 µg of formoterol fumarate dihydrate.

[91] The stable pharmaceutical product according to any one of embodiments [66]-[81], wherein the pharmaceutical composition comprises from about 2969 µg to about 3016 µg of lactose monohydrate per about 1 µg of formoterol.

[92] The stable pharmaceutical product according to any one of embodiments [75]-[91], wherein the sealed package is made of metal, glass, or plastic, and the sealed package is selected from the group consisting of a bottle, a bag, a drum box, and an irregularly shaped container.

[93] The stable pharmaceutical product of embodiment [92], wherein the sealed package is a flexible laminate.

[94] The stable pharmaceutical product according to embodiment [93], wherein the flexible laminate comprises three layers: a protective layer, a heat sealable layer, and a moisture impermeable layer located between the protective layer and the heat sealable layer.

[95] The stable pharmaceutical product according to embodiment [94], wherein the protective layer is polyester, the moisture impermeable layer is a metal selected from the group consisting of aluminum, copper, steel, zinc, iron, tin, magnesium, and a mixture thereof, and the heat sealable layer is polyethylene.

[96] The stable pharmaceutical product of embodiment [95], wherein the moisture impermeable layer is aluminum.

[97] The stable pharmaceutical product according to any one of embodiments [75]-[96], wherein the sealed package is hermetically sealed by heat-sealing, gluing, welding, brazing, mechanical closures, mechanical clamps, or compression.

[98] The stable pharmaceutical product of any of embodiments [75]-[97], wherein the effective amount of the adsorbent material is that amount to prevent or reduce formation of Maillard products.

[99] A stable pharmaceutical product comprising:
  a) a pharmaceutical composition in the solid state comprising formoterol fumarate dihydrate and non-micronized lactose monohydrate having a mean particle size of about 41 µm, wherein the pharmaceutical composition is housed within a dry powder inhaler;
  b) an effective amount of an 10 Å molecular sieve; and
  c) a sealed package substantially impermeable to moisture, wherein the sealed package is a flexible laminate, and the sealed package forms an enclosed volume within which the dry powder inhaler and the adsorbent material are situated.

[100] The stable pharmaceutical product of embodiment [99], wherein the pharmaceutical composition further comprises a second medicament for treating a respiratory disease or disorder.

[101] The stable pharmaceutical product of embodiment [100], wherein the second medicament comprises an anti-inflammatory, a beta2-agonist, an anticholinergic, or a combination thereof.

[102] The stable pharmaceutical product of embodiment [100], wherein the anti-inflammatory comprises a corticosteroid, a mast cell stabilizer, or a leukotriene modifier.

[103] The stable pharmaceutical product of embodiment [100], wherein the corticosteroid is selected from the group consisting of mometasone furoate, triamcinalone acetonide, flunisolide, fluticasone propionate, budesonide, beclomethasone dipropionate, prednisone, betamethasone, cortisone, dexamethasone, hydrocortisone, methylprednisolone, and prednisolone.

[104] The stable pharmaceutical product of embodiment [100], wherein the corticosteroid is ciclesonide.

[105] The stable pharmaceutical product of embodiment [100], wherein the mast cell stabilizer comprises intal, tilade, or a combination thereof.

[106] The stable pharmaceutical product of embodiment [100], wherein the leukotriene modifier comprises zafirlukast, montelukast sodium, zileuton, or a combination thereof

[107] The stable pharmaceutical product according of embodiment [99], wherein the beta2-agonist is selected from the group consisting of salmeterol xinafoate, formoterol, albuterol, and salmeterol.

[108] The stable pharmaceutical product of embodiment [99], wherein the anticholinergic is selected from the group consisting of ipratropium bromide, tiotropium bromide, and a mixture thereof.

[109] The stable pharmaceutical product of any of embodiments [99]-[108], wherein the pharmaceutical composition has a particle size of about 0.1 µm to about 10 µm.

[110] The stable pharmaceutical product of any of embodiments [99]-[109], wherein greater than about 95% of the pharmaceutical composition has a particle size of less than about 5 µm.

[111] The stable pharmaceutical product of any of embodiments [99]-[110], wherein the flexible laminate comprises three layers: a protective layer, a heat sealable layer, and a moisture impermeable layer located between the protective layer and the heat sealable layer.

[112]. The stable pharmaceutical product according to embodiment [111], wherein the protective layer is polyester, the moisture impermeable layer is a metal selected from the group consisting of aluminum, copper, steel, zinc, iron, tin, magnesium, and a mixture thereof, and the heat sealable layer is polyethylene.

[113]. The stable pharmaceutical product according to embodiment [112], wherein the moisture impermeable layer is aluminum.

[114] The stable pharmaceutical product according to any one of embodiments [99]-[113], wherein the flexible laminate is heat-sealed.

[115] The stable pharmaceutical product according to any of embodiments [99]-[114], wherein the pharmaceutical composition comprises about 2969 µg to about 3016 µg of lactose monohydrate per about 0.5 µg to about 4 µg of formoterol fumarate dihydrate.

[116] The stable pharmaceutical product according to embodiment [115], wherein the pharmaceutical composition comprises about 2969 µg to about 3016 µg of lactose monohydrate per about 1 µg to about 2 µg of formoterol.

[117] The stable pharmaceutical product according to embodiment [116], wherein the pharmaceutical composition comprises about 2969 µg to about 3016 µg of lactose monohydrate per about 1 µg of formoterol.

[118] The stable pharmaceutical product of any of embodiments [99]-[117], wherein the effective amount of the adsorbent material is that amount to prevent or reduce formation of Maillard products.

[119] A method for preventing the formation of one or more Maillard products due to a chemical reaction between a medicament of a pharmaceutical product and a reducing sugar, wherein the pharmaceutical product comprises:
  a) a pharmaceutical composition in the solid state comprising the medicament and a reducing sugar;
  b) an effective amount of an adsorbent material; and
  c) a sealed package substantially impermeable to moisture and having an enclosed volume within which the pharmaceutical composition and the adsorbent material are situated;
  wherein the method comprises the steps of:
  (i) positioning an effective amount of the adsorbent material and the pharmaceutical composition within a sealable package;
  (ii) sealing the package to form the sealed package so that the pharmaceutical composition and adsorbent are in an enclosed volume within the sealed package; and
  (iii) adsorbing moisture in the package so as to prevent formation of one or more Maillard products.

[120] The method according to embodiment [119], wherein the pharmaceutical composition is in a dry powder inhaler.

The present invention is also based upon the discovery that, surprisingly and unexpectedly, the presence an excess amount of a hydrophobic material in a stable pharmaceutical product of the present invention substantially maintains the fine particle fraction of a hydrophilic medicament in the stable pharmaceutical product. As a result, aggregation of hydrophilic medicament is limited, and efficient dry powder inhalation administration of fine particles of hydrophilic medicament to the lung of patient can be promoted. Although under no obligation to explain this discovery, and certainly not intending to be bound to any hypothesis that may explain this discovery, it is believed that this protective effect appears to occur when low dose hydrophilic medicaments (such as formoterol fumarate dihydrate) are formulated with an excess amount of a hydrophobic material, (such as a corticosteroid as described above), thereby limiting the potential for interaction of the hydrophilic medicament to the effects of ambient moisture vapor. As a result, greater product performance stability is conferred upon the hydrophilic medicament when combined with an excess amount of hydrophobic material than in the absence of the hydrophobic material. Hence, the present invention further extends to:

[121] A method for substantially maintaining fine particle fraction a hydrophilic medicament for treating a respiratory disease or disorder, comprising the steps of:
   (a) providing a pharmaceutical product that comprises:
      (i) a pharmaceutical composition comprising the hydrophilic medicament and a reducing sugar;
      (ii) an effective amount of an adsorbent material;
      (iii) a sealed package substantially impermeable to moisture having an enclosed volume within which the pharmaceutical composition and the adsorbent material are situated; and
   (b) contacting the hydrophilic medicament in the pharmaceutical composition with a hydrophobic material,
   wherein the ratio of the hydrophobic material to the hydrophilic material is at least 5:1.

[122] The method of embodiment [121], wherein the hydrophilic medicament is a beta2-agonist.

[123] The method of embodiment [122], wherein the beta2-agonist is selected from the group consisting of salmeterol xinafoate, formoterol, and albuterol.

[124] The method embodiment [123], wherein the hydrophilic medicament is formoterol.

[125] The method of any of Embodiments [121]-[124], wherein the hydrophobic material is a hydrophobic medicament for treating a respiratory disease or disorder.

[126] The method of embodiment [125], wherein the hydrophobic medicament is a corticosteroid.

[127] The method of embodiment [126], wherein the corticosteroid is selected from the group consisting of mometasone furoate, triamcinalone acetonide, flunisolide, fluticasone propionate, budesonide, beclomethasone dipropionate, prednisone, betamethasone, cortisone, dexamethasone, hydrocortisone, methylprednisolone, and prednisolone.

[128] The method of embodiment [126], wherein the corticosteroid is ciclesonide.

[129] The method of any of embodiments [121]-[128], wherein the ratio of hydrophobic material to hydrophilic medicament is from about 10:1 to about 100:1.

[130] The method of any of embodiments [121]-[129], wherein the hydrophobic material and the hydrophilic medicament have a particle size of about 0.1 µm to about 10 µm.

[131] The method of any of embodiments [121]-[130], wherein greater than about 95% of the hydrophobic material and the hydrophilic medicament have a particle size of less than about 5 µm.

[132] The method of any of embodiments [121]-[131], wherein the reducing sugar is selected from the group consisting of lactose, glucose, mannose, galactose, maltose, xylose, cellobiose, mellibiose, and maltotriose.

[133] The method of embodiment [132], wherein the reducing sugar is non-micronized.

[134] The method of embodiment [133], wherein the reducing sugar is lactose monohydrate.

[135] The method of any of embodiments [121]-[134], wherein the adsorbent material is selected from the group consisting of a molecular sieve, an activated clay, charcoal, an activated alumina, silica, a zeolite, a bauxite, and a mixture thereof.

[136] The method of any of embodiments [121]-[135], wherein the adsorbent material is 10 Å (Angstrom) molecular sieves.

[137] The method of any of embodiments [131]-[136], wherein the pharmaceutical composition is housed in a dry powder inhaler.

[138] The method of any of embodiments [121]-[137], wherein the sealed package is a flexible laminate.

[139] The method of embodiment [138], wherein the flexible laminate comprises three layers: a protective layer, a heat sealable layer, and a moisture impermeable layer located between the protective layer and the heat sealable layer.

[140] The method of embodiment [139], wherein the protective layer is polyester, the moisture impermeable layer is a metal selected from the group consisting of aluminum, copper, steel, zinc, iron, tin, magnesium, and a mixture thereof, and the heat sealable layer is polyethylene.

[141] The method of embodiment [140], wherein the moisture impermeable layer is aluminum.

[142] The method according to any one of embodiments [121]-[141], wherein the sealed package is hermetically sealed by heat-sealing, gluing, welding, brazing, mechanical closures, mechanical clamps, or compression.

[143] The method of any of embodiments [121]-[142], wherein the effective amount of the adsorbent material is that amount to prevent or reduce formation of Maillard products.

It is appreciated that certain features of the invention, which are, for clarity, described in the context of separate embodiments, may also be provided in combination in a single embodiment. Also, various features of the invention that are, for brevity, described in the context of a single embodiment, may also be provided separately or in any suitable subcombination.

Furthermore, numerous terms and phrases are used throughout the instant Specification and Claims. Accordingly:

The term "stable" as used herein is intended to mean that a medicament of a pharmaceutical product or a method of the present invention does not substantially decompose to form one or more Maillard products when stored in a sealed package with an adsorbent material at 40 degrees Celsius at 75% relative humidity for at least 5 months. For example, there is substantially no Maillard product identified when the medicament is formoterol, and it is stored in a sealed package with an adsorbent material at about 40 degrees Celsius at about 75% relative humidity for at least 5 months.

As used herein, the term "fine particle fraction" is that amount or percentage of the particles of a pharmaceutical composition inhaled into the lung of a patient that have an aerodynamic diameter of about 6 microns or less The "aerodynamic diameter" of a medicament inhaled into the lung of a patient can be approximated for all particles greater than 0.5 microns using the following equation:

$$d_{pa} = d_{ps}\sqrt{\rho_p} \qquad (1)$$

where:
$d_{pa}$=Aerodynamic particle diameter, µm
$d_{ps}$=Stokes diameter, µm
$\rho_p$=Particle density, gm/cm$^3$ As used herein, the term "hydrophobic material" refers to a pharmaceutically acceptable material that tends not to combine with water, or is incapable of dissolving in water. A particular example of such a material is a hydrophobic medicament for treating a respiratory disease or disorder, such as a corticosteroid, e.g. mometasone furoate, flunisolide, triamcinalone acetonide, fluticasone propionate, budesonide, beclomethasone dipropionate, prednisone, betamethasone, cortisone, dexamethasone, hydrocortisone, methylprednisolone, prednisolone, ciclesonide, etc. The hydrophobic material can also be a carrier or excipient in a pharmaceutical composition with the hydrophilic medicament.

As used herein, the phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein, the term "hydrophilic medicament" refers to a medicament that readily absorbs water, or dissolves in water. A particular example of such a medicament having applications herein is a beta2-agonist, such as salmeterol xinafoate, formoterol, and albuterol, to name only a few.

The term "reducing sugar" as used herein means a carbohydrate such as lactose, glucose, mannose, galactose, maltose, xylose, cellobiose, mellibiose, or maltotriose that undergoes oxidation and is able to reduce a metal ion to a lower oxidation state. In a particular embodiment of the present invention, the reducing sugar is lactose. More particularly, the reducing sugar is lactose monohydrate, such as RESPITOSE ML001 (DMV, Veghel, The Netherlands). The particle size of the reducing sugar can be from about 0.5 µm to about 350 µm, from about 0.5 µm to about 315 µm, from about 0.5 µm to about 150 µm, from about 0.5 µm to about 100 µm, from about 0.5 µm to about 45 µm, from about 0.5 µm to about 25 µm, from about 0.5 µm to about 10 µm, from about 5 µm to about 350 µm, from about 5 µm to about 315 µm, from about 5 µm to about 150 µm, from about 5 µm to about 100 µm, from about 5 µm to about 45 µm, from about 5 µm to about 25 µm, from about 51 µm to about 10 µm, from about 10 µm to about 35 µm, from about 10 µm to about 315 µm, from about 10 µm to about 150 µm, from about 10 µm to about 100 µm, from about 10 µm to about 45 µm, from about 10 µm to about 25 µm, from about 25 µm to about 350 µm, from about 25 µm to about 315 µm, from about 25 µm to about 150 µm, from about 25 µm to about 100 µm, from about 25 µm to about 45 µm, from about 45 µm to about 350 µm, from about 45 µm to about 315 µm, from about 45 µm to about 150 µm, from about 45 µm to about 100 µm, from about 100 µm to about 350 µm from about 100 µm to about 315 µm, from about 100 µm to about 150 µm, from about 150 µm to about 350 µm, from about 150 µm to about 315 µm, from about 315 µm to about 350 µm. In particular, the mean particle size is about 41 µm. Also, the reducing sugar need not be micronized. The term "Maillard product" as used herein, means those products that are formed via the Maillard reaction of the medicament with the reducing sugar in the presence of moisture.

Figure 2:
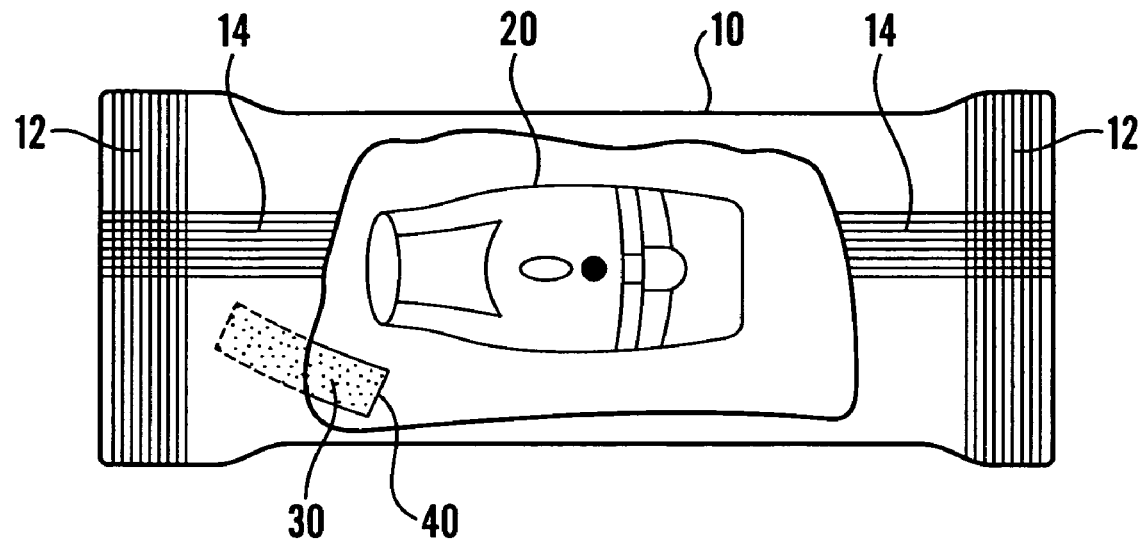
FIG. 2 depicts a typical dry-power inhaler package according to the present invention.
Figure 3:
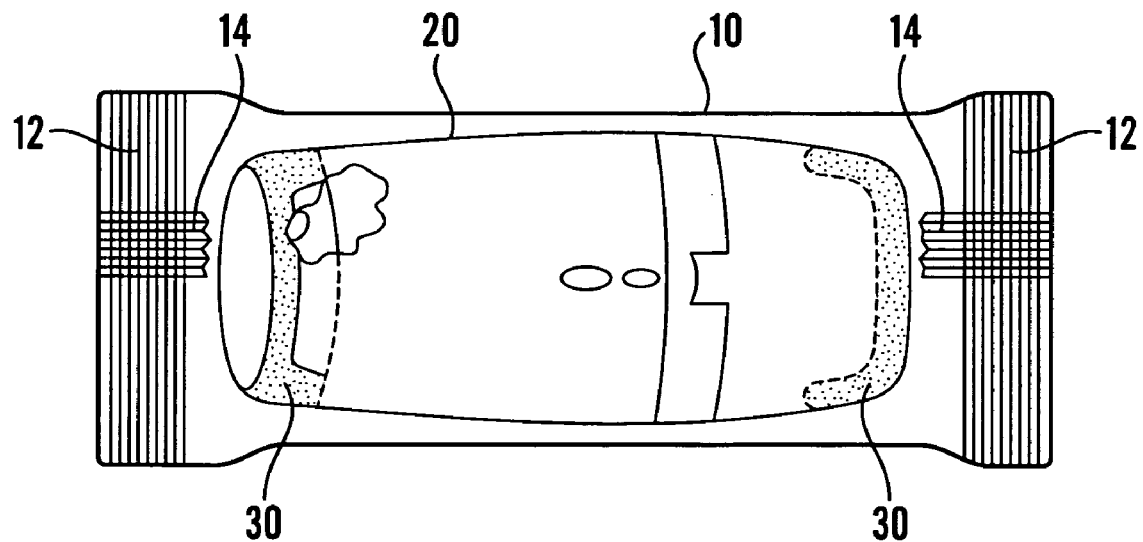
FIG. 3 depicts two of a number of possible locations for the absorbent in a dry-power inhaler. For example, they could possibly be molded as part of one of the plastic components, or could be provided in a container that is fixed to the inhaler.

The term "sealed package" as used herein is meant to encompass a sealed container that is substantially impermeable to moisture. For example, a sealed package may be made of metal, glass, or plastic, and is selected from the group consisting of bottles, bags, drum boxes, and irregularly shaped containers. In a particular embodiment, the package is a conventional flexible package (e.g. an overwrap) and its manufacturing is well within the knowledge of the people skilled in the art. In general, the flexible package is constructed from flat reels of laminate that are folded or otherwise formed according to the packaging equipment technology into a package by means of sealing and cutting. For example, as shown in FIG. 2, the sealed package has a substantially impermeable flexible package 10, in which a dry powder inhaler 20 and a molecular sieve 30 enclosed in a porous sachet 40 are sealed. In this embodiment the package is constructed from a flat reel of flexible material that is curled around into a long tube and a seal 14 is formed by heating (welding) the edges of the tube together. The cross seals 12 are formed by a straight heater bar that clamps the laminate tube before and after the package contents (i.e., the inhaler and the adsorbent sachet). It also cuts the continuous tube into individual packs. As a result, there is a long continuous seal 14 down the middle of the sealed package and the cross seals 12 at both ends. Also, in FIG. 3, the sealed package has a substantially impermeable flexible package 10, in which a dry powder inhaler 20 and adsorbent 30 are situated. The adsorbent 30 can molded as part of one of the plastic components, or could be provided in a container that is fixed to the inhaler. In this embodiment, a sealed package is constructed from a flat reel of flexible material that is curled around into a long tube and a seal 14 is formed by heating (welding) the edges of the tube together. The cross seals 12 are formed by a straight heater bar that clamps the laminate tube before and after the package contents. It also cuts the continuous tube into individual packs. As a result, there is a long continuous seal 14 down the middle of the pack and the cross seals 12 at both ends.

Other sealed package types may include more or less seals according to the desired shape of the container, which may be flat seals or crimped, and may include gussets. The seals may be formed by heating (welding) or by the use of pressure sensitive materials. In a further embodiment the flexible laminates may be formed using heat, pressure and/or vacuum into blisters or pockets to contain the product and which are then sealed by heating.

A flexible sealed package is a particular type of package having applications herein. However, other types of enclosures or containers may be suitable, whether flexible or inflexible, provided that the enclosure chosen is substantially impermeable to moisture ingress.

A particular flexible material for making a flexible sealed package is a laminate, although other materials may also be satisfactorily employed. The main limitation is that the laminate must be substantially impermeable to atmosphere moisture.

The laminate used in making packages generally consists of several layers of materials either co-extruded or bonded together to form an apparently single film of "laminate". As an example, a suitable laminate may have three layers adhesively laminated to each other: protective outer layer, a heat sealable layer, and a moisture impermeable layer located between the protective outer layer and the heat sealable layer. Generally, an adhesive such as a polyester adhesive is located between each of the layers. Numerous materials can be used for the protective layer, including paper or a polymer, such as polyester. The heat sealable layer can also be made of a variety of materials that can undergo heat sealing. For example, Pharmaflex Ltd., part of Alcan inc. (Cramlington, Northumberland, England) supplies a laminate film having three layers: polyester (12 µm), aluminum foil (9 µm) and polyethylene (50 µm) (product catalog LMP-F BRI/72/H1). Also, another suitable laminate consists of polyester (12 µm), aluminium foil (9 µm) and linear low-density polyethylene (40 µm), wherein the three layers are extrusion laminated together using bonding layers that include polyethylene based polymers. This laminate is available from Amcor Flexibles, Lund, Sweden. The heat sealable layer forms the inside of the package (in contact with the medical device) and is normally a thermoplastic layer. A common material for the inner layer is polyethylene, but other polyolefinic or cyclo-olefinic materials may also be used. In addition, specialist materials such as ionomers are also frequently used for making the inner layer, for example, the ionomer under the tradename SURLYN.

The moisture impermeable layer is situated between the inner heat sealable layer and the outer protective layer, and provides impermeability to the pack. Aluminum foil is commonly used for the moisture impermeable layer, although any other metals capable of being rolled into thin sheets can also be satisfactorily used. A typical thickness for the aluminum foil layer is about 8 or 9 microns. Alternatively, the barrier layer may be metalized film, made up of tin, iron, zinc, magnesium or other metals coated by vacuum deposition or sputtering onto a polymeric sheet. In a particular embodiment, aluminum is used as the moisture impermeable layer.

The outer protective layer normally provides support, impact resistance, and protection for the moisture impermeable layer and general robustness to the pack. A commonly used material for the protective layer is polyester, although other material, such as paper, may also be used.

The present invention is intended to encompass the free acids, free bases, salts, amines and various hydrate forms including semi-hydrate forms of such medicaments and is particularly directed towards pharmaceutically acceptable formulations of such medicaments which are formulated in combination with pharmaceutically acceptable excipient materials generally known to those skilled in the art, particularly without other additives such as preservatives. Thus, as used herein, the term "formoterol" refers to any optically active isomer of formoterol, as well as to any hydrate of formoterol. Optionally, a pharmaceutical composition can comprise a medicament or a combination of more than one medicament.

A medicament may also be compounded with a variety of additives, such as surfactants or emulsifiers, and vehicles.

A particular medicament formulation consists essentially of a medicament, or a physiologically acceptable salt or solvate thereof, optionally in combination with one or more other pharmacologically active agents.

Optionally, the formulations according to the invention may further comprise one or more antioxidants. The antioxidant may be selected from the group consisting of tocopherol, methyl paraben, ethyl paraben and ascorbic acid and mixtures thereof. A particular antioxidant is tocopherol.

As used herein, the term "dry powder inhaler" (DPI) refers to a breath activated device for administering a dry powder into the lungs of a subject. Dry powder inhalers having applications herein include, but certainly are not limited to the TWISTHALER produced by Schering Plough Corp., Kenilworth, N.J.; the SPINHALER produced by Fisons, UK; the ROTAHALER produced by GlaxoSmithkline; the ULTRAHALER produced by Aventis Pharma, UK; the TURBUHALER produced by Astrazeneca Corp.; and the ACCUHALER produced by GlaxoSmithkline, to name only a few. A particular dry powder inhaler having applications herein is the ULTRAHALER.

The term "adsorbent" as used herein is meant to encompass a substance that has the ability to condense or hold molecules of other substances on its surface or in its inner structure, an activity often referred as "adsorbing" or "absorbing", respectively. Examples of such adsorbents include activated carbon, alumina, bauxite, charcoal, zeolites, silica gel, molecular sieves, activated clays, bauxite, and mixtures thereof.

The present invention is not limited to any specific adsorbents. Choosing a proper adsorbent for moisture is well within the ordinary skill of the artisans in the field. They can make an initial choice based on their knowledge and experience (for example, weighing the factors such as the pore size of an adsorbent (as well as any electronic charges it carries) and then conduct routine tests to determine the actual effectiveness, and the effective amount, of the chosen adsorbent against a given amount of moisture. They may need to repeat the process until a proper adsorbent is found. One of the tests for finding an effective adsorbent against Maillard product formation is described herein and can be adopted by people skilled in the art to determine the actual effectiveness of any adsorbent, currently existing or to be developed in the future, against formation of Maillard product caused by the interaction of the medicament and reduced sugar, in the presence of moisture.

There are numerous ways in which the absorbent material can be present in the pharmaceutical product. For example, the adsorbent can be incorporated into a polymer mixture and manufactured into a plastic component of the medical device. Also, the adsorbent can be incorporated into a polymer mixture and manufactured into plastic sheeting used in the packaging of the device. The adsorbent can be incorporated into a polymer mixture in the same, or similar, manner as desiccant polymer mixtures disclosed in U.S. Pat. Nos. 5,911,937; 3,245,946; 4,013,566; 4,407,897; 4,425,410; 4,464,443; 5,078,909; and 4,792,484, which are incorporated herein by reference in their entireties. Although these patents disclose desiccants, it is foreseeable that the methods of manufacturing these plastics could be used to manufacture an adsorbent material used in the present invention. For example, the adsorbent can be within a cavity in the medical device (i.e. housed in the device) e.g. the adsorbent can be situated inside the cap or inside the body of a dry-powder inhaler (see FIG. 3). Also, the adsorbent can be a component of the device e.g. the cap of a dry-powder inhaler can comprise an adsorbent polymer mixture (see FIG. 3). Also, the adsorbent can be affixed to the device in the form of an adhesive sticker/tape comprising the adsorbent. Furthermore, the adsorbent can be separate from the device in an enclosed volume within which the device is situated (see FIG. 2).

The adsorbent can also be in the form of an adsorbent incorporated into an adhesive (e.g. a self-adhesive patch or tape), in the same, or similar, manner as adhesive desiccants disclosed in U.S. Pat. No. 6,103,141, which is incorporated herein by reference in its entirety.

The adsorbent material of the invention can also be in the form of an adsorbent in a porous sachet. Although it is not necessary to have a sachet to contain the adsorbent within the package, a sachet clearly has applications herein. The adsorbent sachets are commercially available from many suppliers including Sud-Chemie (Middlewich, England). The sachet, with a "tea-bag" like appearance, is generally manufactured from synthetic fibers, such as polyamide or polyester fibers or blends thereof. Commercially available materials suitable for making adsorbent sachets include, for example, GDT-II from San-ei Corporation (Osaka, Japan) and Tyvek from Perfecseal (Londonderry N. Ireland U.K.). However, a suitable sachet may be in other convenient shapes or appearances and made from other permeable materials. Examples of adsorbents are selected from the group consisting of molecular sieves, activated clays, activated alumina, silica, zeolites, bauxites, and mixtures thereof. In a particular embodiment, the adsorbent material is 10 Å (Angstrom) molecular sieves. The amount of sieves to be used in the invention can be readily calculated by a person skilled in the art, for example by taking into consideration the amount of moisture to be absorbed, the pore size of the molecular sieve and the internal volume of the package. In a particular embodiment of the present invention, about 0.8 grams to about 10 grams of molecular sieves is an effective amount, and more particularly, 0.8 grams to about 4.0 grams is an effective amount. Molecular sieve material is commercially available from several manufacturers. For example AtoFina (Solihull, England) market a molecular sieve under the trade name of Siliporite. More detailed technical information about molecular sieves and their other industrial uses can be found in the Molecular Seives: Unique Moisture and Odor-Taste Control Material", D. Hajdu, T. J. Dangieri and S. R. Dunne, *TAPPI Polym., Laminations Coat. Conf.* (1999), Vol. 2, p. 655-662, which is incorporated herein by reference in its entirety.

The term "effective amount of an adsorbent material" as used herein is intended to encompass the amount of an adsorbent material that is necessary to be effective in reducing formation of Maillard products. The effective amount of adsorbent will depend on a number of factors, including the type of adsorbent and the moisture content of the pharmaceutical product. A person skilled in the art would readily be able to determine the effective amount of the adsorbent.

While there have been described and pointed out fundamental novel features of the invention as applied to a particular embodiment thereof, it will be understood that various omissions and substitutions and changes, in the form and details of the packages, adsorbents, pharmaceutical products and methods illustrated, may be made by those skilled in the art without departing from the spirit of the invention. For example, it is expressly intended that all combinations of those elements and/or method steps which perform substantially the same function in substantially the same way to achieve the same results are within the scope of the invention.

The present invention may be better understood by reference to the following non-limiting Examples, which are provided as exemplary of the invention. The following Examples are presented in order to more fully illustrate particular embodiments of the present invention. They should in no way be construed, however, as limiting the broad scope of the present invention.

EXAMPLE I

Preparation of a Stable Pharmaceutical Product of the Invention

A. Stable Pharmaceutical Product Comprising and Formoterol Fumarate Dihydrate and an Additional Medicament The additional medicament of this example can be any medicament discussed above.

1. Deaggregate lactose monohydrate, formoterol fumarate dihydrate, and the additional medicament (separately).
2. Add both the lactose monohydrate and the additional medicament into the mixing drum of a high shear mixer.
3. Mix composition using a blender for about 4 minutes.
4. Remove a portion of the powder (e.g. 100 g) and add to formoterol fumarate dihydrate.
5. Blend the formoterol fumarate dihydrate with the additional medicament/lactose mixture in a blender.
6. Return the pre-blend to the remainder of the blend in the high-shear mixer.
7. Blend for a further e.g. 4 minutes.
8. Fill the blend into a dry powder inhalation device using a suitable filling machine.
9. Wrap the dry powder inhalation device with molecular sieves inside a laminate foil overwrap (i.e. package).

Stability Testing

Using the procedure discussed above, and ciclesonide as the additional medicament, a blend of ciclesonide (19.97 mg/g), formoterol fumarate dihydrate (0.3 mg/g) and lactose monohydrate (979.70 mg/g) were blended in a mixer for several minutes. The blend was filled into an Aventis ULTRAHALER dry powder inhalation device using a filling machine, and the device was wrapped in a laminate foil overwrap with a molecular sieve sachet. The product was stored at 40 degrees Celsius and 75% relative humidity, for 10 weeks and the amount of degradation measured by HPLC using the following analytical conditions:

| Column: | Hipersil BDS-C18, 5 µm particle size, 150 mm × 4.6 mm i.d. |
|---|---|
| Column temperature: | Ambient |
| Mobile phase A composition: | 30% Ammonium Acetate (pH 8.0 ± 0.05), 55% Water, 159 Acetonitrile |
| Mobile phase B composition: | 300 Ammonium Acetate (pH 8.0 ± 0.05): 750 Acetonitrile |
| Gradient Time Table | Time (min) | % A | % B |
| | 0 | 100 | 0 |
| | 10 | 100 | 0 |
| | 20 | 87 | 13 |
| | 30 | 70 | 30 |
| | 40 | 70 | 30 |
| | 40.1 | 0 | 100 |
| | 53.0 | 0 | 100 |
| | 53.1 | 100 | 0 |
| Flow rate: | 1.0 ml/minute |
| Detection: | 250 nm |
| Injection volume: | 200 µl |
| Total run time (time between 2 injections): | 60 minutes |
| Typical retention time of formoterol fumarate dihydrate | Approximately 18 to 19 minutes |

Results:

Only two degradants, above the reporting threshold, were formed on storage at Relative Retention Time (RRT)=1.35 and RRT 1.82 at levels of 1.42 and 1.01% area respectively (these were identified as non-Maillard products). This is in stark contrast to 8 degradants that were identified when the same product is stored at 40 degrees Celsius and 75% relative humidity, without an overwrap and molecular sieve. The largest degradant observed was at RRT=1.12 (1.42% area) in the product stored at 40 degrees Celsius and 75% relative humidity without an overwrap and molecular sieve. The results of this stability test are shown in FIG. 1.

The above study result demonstrates that inclusion of an adsorbent material and the substantially moisture impermeable sealed package is a simple and effective solution to the problem of Maillard product formation occurring when a medicament and reducing sugar in a dry powder inhaler are in contact with each other in the presence of moisture. Particularly, molecular sieves are effective adsorbent materials against Maillard product formation caused by Formoterol and lactose in the presence of moisture.

B. Stable Pharmaceutical Product of Formoterol Fumarate Dihydrate

In this example, a pharmaceutical product having only formoterol fumarate dihydrate as the medicament was produced with a reducing sugar. A process for producing a total quantity of 20 kg blend that contains 5.4 g of formoterol fumarate dihydrate and 19994.6 g of lactose monohydrate is as follows:

Blending Process
1. Lactose monohydrate and formoterol fumarate dihydrate are screened to remove aggregate particles.
2. The required quantities of each material are weighed out.
3. 5.4 g of formoterol fumarate dihydrate and approximately 100 g of the deaggregated lactose monohydrate are blended to form a "pre-blend".
4. The pre-blend is then added to the remaining 19894.6 g of lactose monohydrate in a blender. The powder mix is blended to form a final homogeneous powder blend.

Manufacture of Formoterol DPI ULTRAHALERs

The final powder blend is filled into dry powder inhaler (DPI) components using a purpose-built mechanical filling and assembly machine.

In a particular embodiment, the DPI filled with this stable pharmaceutical product is the ULTRAHALER from Aventis Pharma, UK. After being filled, the ULTRAHALER was overwrapped with a laminate foil overwrap to form a sealed package. A sachet containing about 4 g of molecular sieves was also contained within the sealed package. Pursuant to the present invention, the level of impurities that develop within the DPI due to the Maillaird reaction clearly are less than the levels of impurities that develop in absence of the laminate foil overwrap and the molecular sieves. Data to support this observation are set forth in Table 1 below, which shows a similar extent of degradation after 2 and 6 months storage at 25° C./75% RH when stored without an overwrap and sieve and when stored with these components, respectively.

TABLE 1

| Product | Assay mg/g (% of nominal) | | |
|---|---|---|---|
| | Initial | 2 months | 6 months |
| Formoterol fumarate 4.5 mcg/actuation inside overwrap containing molecular sieve | 0.255 (100) | | 0.240 (94) |
| Formoterol fumarate 4.5 mcg/actuation | 0.255 (100) | 0.223 (87) | |

Although there are various types of adsorbent materials available and their effectiveness against any given gaseous substance varies considerably, it is understood that people of ordinary skill in the art can easily adopt the above-described example to determine the type and the amount of an adsorbent material that is effective in reducing formation of medicament adducts for any other types medical devices containing other different medicaments.

EXAMPLE II

Presence of Excess Hydrophobic Medicament Protects the Fine Particle Fraction of a Hydrophilic Medicament In this example, ciclesonide was used as the hydrophobic medicament, and formoterol fumarate dihydrate was used as the hydrophilic medicament. Three separate ULTRAHALERs were filled, respectively, with three separate formulations of ciclesonide and formoterol fumarate dihydrate. The three formulations are:

(1) 80 mcg ciclesonide: 4.5 mcg formoterol fumarate dihydrate per actuation (ratio of about 20:1);
(2) 160 mcg ciclesonide: 4.5 mcg formoterol fumarate dihydrate per actuation (ratio of about 40:1); and
(3) 320 mcg ciclesonide: 4.5 mcg formoterol fumarate dihydrate (ratio of about 80:1).

An ULTRAHALER filled with the control formulation of 4.5 mcg formoterol fumarate dihydrate was also prepared. Each of these ULTRAHALERs was overwrapped with a sealed protective foil overwrap that also contained a sachet of molecular sieves.

Initially, the percentage of fine particle fraction (mass<5.8 microns, expressed as a % of dose) was measured in each ULTRAHALER DPI before its removal from the overwrap (initial measurement). The ULTRAHALERs were then stored for two (2) months at conditions of 25° C., 75% relative humidity (RH). The percentage of fine particle fraction was measured in each ULTRARALER at one month and two months. These measurements are set forth in Table 2 below:

TABLE 2

| Formulation | Timepoint | | |
|---|---|---|---|
| | Initial | 1 month | 2 months |
| | Formoterol Fumarate Fine Particle Fraction (%) | | |
| 80 mcg ciclesonide: 4.5 mcg formoterol fumarate/actuation | 35 | 33 | 31 |
| 160 mcg ciclesonide: 4.5 mcg formoterol fumarate/actuation | 32 | 40 | 32 |
| 320 mcg ciclesonide: 4.5 mcg formoterol fumarate/actuation | 32 | 40 | 36 |
| 4.5 mcg formoterol fumarate (mono) | 33 | 23 | 19 |

According to the data of Table 2, the fine particle fraction of formoterol fumarate dihydrate in the presence of ciclesonide remained comparable (in one case equal and in another even greater), with the initial measurement taken from an ULTRAHALER within the laminate overwrap with a sachet of molecular sieves, even after two months the ULTRAHALER had been removed from the overwrap and stored at 25° C., 75% relative humidity. In contrast, the formoterol fumarate dihydrate fine particle fraction in the control formulation that lacked ciclesonide decreased approximately 42% as compared to its initial measurement.

This example demonstrates that the presence of a hydrophobic medicament in an excess of 5:1 with respect to the presence of a hydrophilic medicament in a pharmaceutical composition substantially protects the fine particle fraction of hydrophilic medicament following the removal a dry powder inhaler containing the pharmaceutical composition from a sealed package that also contains an adsorbent material.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A method for substantially maintaining fine particle fraction of formoterol fumarate dihydrate in a pharmaceutical product for treating a respiratory disease or disorder, comprising the steps of:
    (a) providing a pharmaceutical product that comprises:
        (i) a pharmaceutical composition in the solid state comprising formoterol fumarate dihydrate and a reducing sugar;
        (ii) an effective amount of an adsorbent material;
        (iii) a sealed package substantially impermeable to moisture having an enclosed volume within which the pharmaceutical composition and the adsorbent material are situated; and
    (b) contacting formoterol fumarate dihydrate in the pharmaceutical composition with ciclesonide, wherein the ratio of the ciclesonide to formoterol fumarate dihydrate is at least 5:1.

2. The method of claim 1, wherein the ratio of ciclesonide to formoterol fumarate dihydrate is from about 10:1 to about 100:1.

3. The method of claim 1, wherein the ciclesonide and the formoterol fumarate dihydrate have a particle size of about 0.1 µm to about 10 µm.

4. The method of claim 1, wherein greater than about 95% of the ciclesonide and the formoterol fumarate dihydrate have a particle size of less than about 5 µm.

5. The method of claim 1, wherein the reducing sugar is selected from the group consisting of lactose, glucose, mannose, galactose, maltose, xylose, cellobiose, mellibiose, and maltotriose.

6. The method of claim 1, wherein the adsorbent material is selected from the group consisting of a molecular sieve, an activated clay, charcoal, an activated alumina, silica, a zeolite, a bauxite, and a mixture thereof.

7. The method of claim 1, wherein the adsorbent material is 10 Å (Angstrom) molecular sieves.

8. The method of claim 1, wherein the sealed package is a flexible laminate.

9. The method according to claim 1, wherein the sealed package is hermetically sealed by heat-sealing, gluing, welding, brazing, mechanical closures, mechanical clamps, or compression.

10. The method of claim 1, wherein the effective amount of the adsorbent material is that amount to eliminate or reduce formation of Maillard products.

11. The method of claim 1, wherein the reducing sugar is lactose.

12. The method of claim 1, wherein the reducing sugar is lactose monohydrate.

13. The method of claim 12, wherein the lactose monohydrate is non-micronised.

14. The method of claim 1, wherein the pharmaceutical composition is housed within a dry powder inhaler.

15. The method of claim 14, wherein said adsorbent material is incorporated into a polymer mixture and manufactured into a plastic component of said dry powder inhaler.

16. The method of claim 1, wherein said adsorbent material is incorporated into an adhesive.

17. The method of claim 1, wherein said adsorbent material is in a porous sachet.

18. A method for substantially maintaining fine particle fraction of formoterol fumarate dihydrate in a pharmaceutical product for treating a respiratory disease or disorder, comprising the steps of:
    (a) providing a pharmaceutical product that comprises:
        (i) a pharmaceutical composition in the solid state comprising formoterol fumarate dihydrate and a reducing sugar;
        (ii) an effective amount of an adsorbent material;
        (iii) a sealed package substantially impermeable to moisture having an enclosed volume within which the pharmaceutical composition and the adsorbent material are situated; and
    (b) contacting formoterol fumarate dihydrate in the pharmaceutical composition with ciclesonide, wherein the ratio of the ciclesonide to formoterol fumarate dihydrate is at least 5:1, wherein the fine particle fraction of formoterol fumarate dihydrate has a diameter of 6 µm or less.

19. The method of claim 18, wherein the ratio of ciclesonide to formoterol fumarate dihydrate is from about 10:1 to about 100:1.

20. The method of claim 18, wherein greater than about 95% of the ciclesonide and the formoterol fumarate dihydrate have a diameter of less than about 5 µm.

21. The method of claim 18, wherein the reducing sugar is selected from the group consisting of lactose, glucose, mannose, galactose, maltose, xylose, cellobiose, mellibiose, and maltotriose.

22. The method of claim 18, wherein the adsorbent material is selected from the group consisting of a molecular sieve, an activated clay, charcoal, an activated alumina, silica, a zeolite, a bauxite, and a mixture thereof.

23. The method of claim 18, wherein the adsorbent material is 10 Å (Angstrom) molecular sieves.

24. The method of claim 18, wherein the sealed package is a flexible laminate.

25. The method according to claim 18, wherein the sealed package is hermetically sealed by heat-sealing, gluing, welding, brazing, mechanical closures, mechanical clamps, or compression.

26. The method of claim 18, wherein the effective amount of the adsorbent material is that amount to eliminate or reduce formation of Maillard products.

27. The method of claim 18, wherein the reducing sugar is lactose.

28. The method of claim 18, wherein the reducing sugar is lactose monohydrate.

29. The method of claim 28, wherein the lactose monohydrate is non-micronised.

30. The method of claim 18, wherein the pharmaceutical composition is housed within a dry powder inhaler.

31. The method of claim 30, wherein said adsorbent material is incorporated into a polymer mixture and manufactured into a plastic component of said dry powder inhaler.

32. The method of claim 18, wherein said adsorbent material is incorporated into an adhesive.

33. The method of claim 18, wherein said adsorbent material is in a porous sachet.

* * * * *